United States Patent [19]

Zukosky et al.

[11] Patent Number: 4,525,531

[45] Date of Patent: Jun. 25, 1985

[54] POLYMERIC COMPOSITIONS SUITABLE FOR USE IN THE MEDICAL FIELD AND CONTAINING A POLYOLEFIN, A POLYSILOXANE AND AN ELASTOMER

[75] Inventors: Mimzee Zukosky, Redwood City; Ronald L. Dieck, Sunnyvale, both of Calif.

[73] Assignee: Raychem Corporation, Menlo Park, Calif.

[21] Appl. No.: 488,861

[22] Filed: Apr. 26, 1983

[51] Int. Cl.³ .................... C08L 9/06; C08L 53/02
[52] U.S. Cl. ........................ 525/92; 525/89; 525/101; 525/98
[58] Field of Search ............ 525/89, 92, 101, 98, 525/105, 106

[56] References Cited

U.S. PATENT DOCUMENTS

| | | | |
|---|---|---|---|
| 3,189,662 | 6/1965 | Vaughn | 260/824 |
| 3,664,959 | 5/1972 | Gaines et al. | 525/106 |
| 3,969,308 | 7/1976 | Penneck | 525/101 |
| 4,265,801 | 5/1981 | Moody et al. | 525/106 |
| 4,350,795 | 9/1982 | Bohm et al. | 525/194 |
| 4,386,179 | 5/1983 | Sterling | 524/269 |

FOREIGN PATENT DOCUMENTS

| | | | |
|---|---|---|---|
| 0000583 | 2/1979 | European Pat. Off. | 525/101 |
| 2016482 | 9/1979 | United Kingdom | 525/92 |

OTHER PUBLICATIONS

WO80/00061, Jan. 24, 1980, PCT.

*Primary Examiner*—Wilbert J. Briggs, Sr.
*Attorney, Agent, or Firm*—Timothy H. P. Richardson; Herbert G. Burkard

[57] ABSTRACT

Polymeric compositions comprising 5–60%, preferably 12 to 40%, of a thermoplastic olefin polymer, 1–10%, preferably 2 to 6%, of a siloxane polymer and 30–94%, preferably 58 to 86%, of an elastomer. The olefin polymer can be polyethylene or a polar ethylene copolymer. The siloxane polymer can contain polycarbonate blocks. The elastomer can be an amorphous polyamide of low crystallinity, a thermoplastic elastomer, an ionomer, or a styrene/butadiene copolymer. The compositions are particularly useful in the medical field, for example in the form of tubing.

2 Claims, No Drawings

POLYMERIC COMPOSITIONS SUITABLE FOR USE IN THE MEDICAL FIELD AND CONTAINING A POLYOLEFIN, A POLYSILOXANE AND AN ELASTOMER

BACKGROUND OF THE INVENTION

1. Field of the Invention

This invention relates to new polymeric compositions and their use as shaped products.

2. Introduction to the Invention

There is a continuing need for new polymeric compositions which have desired new combinations of physical and chemical properties or which provide more economical replacements for existing polymeric compositions. For example plasticized polyvinyl chloride (PVC) has many useful properties, but migration of the plasticizer into adjacent surfaces limits its use, for example in the medical field. The so-called "soft" elastomers such as the ABA block copolymers (polystyrene/-polybutadiene/polystyrene block copolymers such as "Kraton" and "Solprene") have many useful properties, but their surface has a high coefficient of friction to human skin, making them unsuitable for use in many medical applications, e.g. as catheter shaft materials or cuffs on endotracheal tubes. Siloxanes have many useful properties, but are expensive.

SUMMARY OF THE INVENTION

We have now discovered new polymer blends which provide new combinations of desired properties, or are functionally similar to, but substantially cheaper than, known polymeric compositions.

The compositions of the invention comprise (a) 5 to 60% of a thermoplastic polymer comprising units derived from an olefin, (b) 1 to 10% of a polymer comprising siloxane units, and (c) 39 to 94% of an elastomer having a Shore D Hardness of less than 60, preferably less than 45 the amounts of components (a), (b) and (c) being by weight, based on the total weight of (a), (b) and (c), subject to the proviso that if the elastomer (c) is a polystyrene/polybutadiene/polystyrene block copolymer, at least one of the following conditions is fulfilled:

(1) the polymer (a) is a polar copolymer, (2) the polymer (b) comprises at least 10% by weight of carbonate units, (3) the composition comprises a radiation cross-linking agent, and (4) the composition has been radiation crosslinked.

DETAILED DESCRIPTION OF THE INVENTION

The relative proportions of the polymers (a), (b) and (c) play an important part in determining the properties of the blends. The siloxane polymer (b) preferably provides 2 to 8%, e.g. 2 to 6%, of the blend. In the absence of a sufficient quantity of the siloxane polymer (b), the composition is difficult to process and the polymers (a) and (c) do not become adequately mixed under normal processing conditions; in addition the tactile properties of the composition are unsatisfactory for many purposes, especially in the medical field. The thermoplastic polymer (a) preferably provides 10 to 50%, particularly 12 to 40%, of the blend. The elastomer (c) preferably provides 48 to 88%, particularly 55 to 86%, of the blend. When the composition is to be used for medical purposes, in which its tactile properties in contact with human skin or other living material is important, the blend preferably contains 15 to 25%, especially 17 to 22%, of polymer (a), 2 to 8% of polymer (b), and 67 to 85%, especially 70 to 81% of polymer (c).

Suitable thermoplastic polymers for use as component (a) of the novel compositions include polyolefins, particularly polyethylene (low density, linear low density, medium density and high density) and polypropylene, and copolymers of olefins, particularly ethylene, with one or more polar comonomers, particularly vinyl acetate, ethyl acrylate, methyl acrylate and methyl methacrylate.

Suitable siloxanes for use as component (b) of the novel compositions include polymers consisting essentially of siloxane units, polymers comprising siloxane units and at least 10% by weight of carbonate units and block copolymers which are solid at room temperature and which comprise polysiloxane and polycarbonate blocks, particularly copolymers comprising poly(dimethylsiloxane) blocks and polycarbonate blocks, such as that sold by General Electric under the trade name "Copel".

Suitable elastomers for use as component (c) of the novel compositions include the following polymers:

(1) Amorphous polyamides, especially the higher polyamides such as Nylon-11 and Nylon-12, having a crystallinity less than 35%, particularly less than 20%. Such polymers usually have a Shore D hardness of about 40.

(2) Ionomers, in particular the metal salts of ethylene/methacrylic acid copolymers sold by du Pont under the tradename "Surlyn". Ionomers usually have a Shore D hardness of about 40.

(3) Styrene/butadiene copolymers, in particular polystyrene/polybutadiene/polystyrene block copolymers such as those sold under the trade names "Kraton" and "Solprene". Such polymers are substantially softer than those in categories (1) and (2) above and usually have a Shore A hardness of 30 to 70.

(4) Thermoplastic elastomers which consist essentially of a multiplicity of recurring short chain ester units and long chain ester units joined through ester linkages, said short chain ester units amounting to 15 to 75 percent by weight of said copolyester and being of the formula

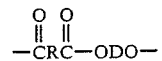

and said long chain ester units amounting to about 25 to 85 percent by weight of said copolyester and being of the formula

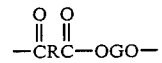

wherein R is the divalent aromatic radical remaining after removal of the carboxyl groups from aromatic dicarboxylic acid having a molecular weight of less than about 350, D is the divalent radical remaining after removal of the hydroxyl groups from organic diol having a molecular weight of less than 250, and G is the divalent radical remaining after removal of the terminal hydroxyl groups from a long chain glycol having an average molecular weight of 350 to 6000, said copolyester having a melt index of less than 150 and a melting point of at least 125° C., for example the polymers sold by du Pont under the trade name "Hytrel". Such polymers usually have a Shore D hardness of about 40.

The various polymers and the amounts thereof can be selected to obtain compositions of preferred properties. We have found the invention to be particularly useful for producing compositions having the following properties:

(1) A tensile strength of 2,500 to 3,500 psi and an elongation of 500 to 625%; these compositions are similar to plasticized PVC in functional properties but do not contain plasticizer, which (as noted above) is liable to migrate.

(2) A tensile strength of 550 to 1,500 psi and an elongation of 360 to 480%; these compositions are similar to polysiloxanes in functional properties but are substantially cheaper.

(3) A tensile strength of 1,000 to 2,000 psi and an elongation of at least 650%; these compositions are similar to conventional "soft" elastomers but have improved tactile properties, especially for medical uses.

The elongations and tensile strength referred to herein are measured by ASTM D-412 at room temperature and at a cross-head speed of 20 inches/minute.

The compositions of the inventions can be shaped in any desired way, preferably by melt-shaping, particularly melt-extrusion. The resulting shaped articles can be used as such, or, for a number of uses, can be cross-linked, preferably by radiation (usually after addition of at least 0.5% of a radiation cross-linking agent such as triallyl isocyanurate). The cross-linking agent is usually added to the polymer blend before it is shaped. The cross-linked articles can be rendered heat-recoverable by deformation above the melting point of the thermoplastic polymer, followed by cooling in the deformed condition, as is well known.

Compositions comprising elastomers in categories 1 and 4 above can readily be cross-linked, but do not have good tactile properties. Compositions comprising elastomers in category (3) above are more difficult to cross-link to a level adequate for the preparation of useful heat-recoverable articles (an $M_{100}$ value above the melting point of the thermoplastic of at least 35 psi is essential). However, we have obtained good results by combining elastomers in category (3) with linear low density polyethylene (which gives compositions having excellent tactile properties) and high density polyethylene. We have also found that use of a siloxane polymer containing polycarbonate segments results in better heat-recoverable articles than polymers which contain only siloxane units.

The compositions of the invention can contain other ingredients such as antioxidants and other stabilisers, fire-retardants, and conductive and non-conductive fillers. For example, where polymer (c) is a siloxane, it may contain 30-70% of a filler, e.g. fumed silica, to assist in obtaining good mixing of the polymers.

EXAMPLES

The invention is illustrated in the following Examples, which are summarized in Tables 1-7 below. In each Example, the ingredients and the amounts thereof, in parts by weight, indicated in the Tables, and also (in each Example, though not given in the Table) 0.3 parts of an antioxidant and 1.5 parts of triallyl isocyanurate, were mixed together on a heated (170°-190° C.) mill, about 20-30% of the elastomer being added first, then the siloxane polymer, then about 70-80% of the olefin polymer, then the remainder of the elastomer, and finally the remainder of the olefin polymer. The mixture was stripped from the mill and pressed into slabs 6"×6" and about 25 mils thick. As noted in the Tables, some of the slabs were tested without crosslinking and others were tested after they had been cross-linked to a dose of 15 Mrad.

In the Tables below, the polymers are identified by their trade names; they are further described below.

Thermoplastic Polymers

PROFAX is polypropylene.
DPDA 6181 is an ethylene/ethyl acrylate copolymer.
MARLEX 6003 is a high density polyethylene.
SCLAIR 8405 UV is linear low density polyethylene.
ELVAX 460 is an ethylene/vinyl acetate copolymer.
GULF 2205 is an ethylene/methyl acrylate copolymer.

Siloxane Polymers

SWS 154 is a methyl vinyl siloxane free from fillers.
SWS 721 is a methyl vinyl siloxane containing a substantial proportion of fumed silica dispersed therein.
GE 5530 and GE 3320 are block copolymers of a polycarbonate and a dimethyl siloxane (see U.S. Pat. No. 3,189,662, the disclosure of which is incorporated by reference herein).

Elastomers

HUELS X 4003 is a Nylon 12.
HYTREL 4056 is a polyester elastomer as defined above, and
KRATON G 2705 is a polystyrene/polybutadiene/polystyrene elastomer.

TABLE 1

| EXAMPLE NO. | | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| PROFAX | | 0 | 0 | 0 | 0 | 0 | 0 | 0 | 0 | 0 | 0 | 0 | 0 | 17 | 17 | 17 |
| DPDA | 6181 | 0 | 0 | 0 | 0 | 0 | 0 | 0 | 0 | 0 | 17 | 17 | 17 | 0 | 0 | 0 |
| MARLEX | 6003 | 0 | 0 | 0 | 0 | 0 | 0 | 17 | 17 | 17 | 0 | 0 | 0 | 0 | 0 | 0 |
| SCLAIR | 8405UV | 0 | 0 | 0 | 17 | 17 | 17 | 0 | 0 | 0 | 0 | 0 | 0 | 0 | 0 | 0 |
| ELVAX | 460 | 17 | 17 | 17 | 0 | 0 | 0 | 0 | 0 | 0 | 0 | 0 | 0 | 0 | 0 | 0 |
| SWS | 721 | 0 | 0 | 3 | 0 | 0 | 3 | 0 | 0 | 3 | 0 | 0 | 3 | 0 | 0 | 3 |
| GE | 5530 | 0 | 3 | 0 | 0 | 3 | 0 | 0 | 3 | 0 | 0 | 3 | 0 | 0 | 3 | 0 |
| GE | 3320 | 3 | 0 | 0 | 3 | 0 | 0 | 3 | 0 | 0 | 3 | 0 | 0 | 3 | 0 | 0 |
| KRATON | G2705 | 78.2 | 78.2 | 78.2 | 78.2 | 78.2 | 78.2 | 78.2 | 78.2 | 78.2 | 78.2 | 78.2 | 78.2 | 78.2 | 78.2 | 78.2 |
| UNBEAMED TEST DATA | | | | | | | | | | | | | | | | |
| TENSILE PSI | | 1632 | 1584 | 1864 | 2490 | 2429 | 2564 | 2203 | 2309 | 2315 | 1452 | 1605 | 1478 | 2402 | 2642 | 2397 |
| % ELONGATION | | 735 | 760 | 810 | 815 | 790 | 815 | 780 | 815 | 785 | 685 | 795 | 780 | 720 | 740 | 695 |
| BEAMED TEST DATA | | | | | | | | | | | | | | | | |
| TENSILE PSI | | | | | 1655 | 1692 | 1593 | 1507 | 1742 | 2359 | | | | 1358 | 1558 | 1306 |
| % ELONGATION | | | | | 730 | 800+ | 780 | 630 | 730 | 720 | | | | 595 | 645 | 590 |

TABLE 1-continued

| EXAMPLE NO. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| M100 PSI | | | | 13 | 12 | 10 | 15 | 15 | 19 | | | | 1 | 0 | 0 |

TABLE 2

| EXAMPLE NO. | | 16 | 17 | 18 | 19 | 20 | 21 | 22 | 23 | 24 | 25 | 26 | 27 |
|---|---|---|---|---|---|---|---|---|---|---|---|---|---|
| DPDA | 6181 | 0 | 0 | 0 | 0 | 0 | 0 | 0 | 0 | 0 | 17 | 17 | 17 |
| MARLEX | 6003 | 0 | 0 | 0 | 0 | 0 | 0 | 17 | 17 | 17 | 0 | 0 | 0 |
| SCLAIR | 8405UV | 0 | 0 | 0 | 17 | 17 | 17 | 0 | 0 | 0 | 0 | 0 | 0 |
| ELVAX | 460 | 17 | 17 | 17 | 0 | 0 | 0 | 0 | 0 | 0 | 0 | 0 | 0 |
| SWS | 721 | 0 | 0 | 3 | 0 | 0 | 3 | 0 | 0 | 3 | 0 | 0 | 3 |
| GE | 5530 | 0 | 3 | 0 | 0 | 3 | 0 | 0 | 3 | 0 | 0 | 3 | 0 |
| GE | 3320 | 3 | 0 | 0 | 3 | 0 | 0 | 3 | 0 | 0 | 3 | 0 | 0 |
| HYTREL | | 78.2 | 78.2 | 78.2 | 78.2 | 78.2 | 78.2 | 78.2 | 78.2 | 78.2 | 78.2 | 78.2 | 78.2 |
| UNBEAMED TEST DATA | | | | | | | | | | | | | |
| TENSILE PSI | | 2834 | 3765 | 3616 | 3137 | 2442 | 3692 | 2626 | 3140 | 3428 | 3035 | 2990 | 3047 |
| % ELONGATION | | 775 | 850 | 845 | 855 | 740 | 885 | 720 | 830 | 815 | 775 | 770 | 765 |
| BEAMED TEST DATA | | | | | | | | | | | | | |
| TENSILE PSI | | 2127 | 2667 | 2617 | 2752 | 2506 | 3217 | 3575 | 4476 | 4057 | 2661 | 2771 | 1981 |
| % ELONGATION | | 440 | 520 | 490 | 450 | 650 | 580 | 560 | 550 | 530 | 500 | 550 | 620 |
| M100 PSI | | 56 | 60 | 66 | 56 | 55 | 50 | 70 | 55 | 52 | 47 | 40 | 49 |

TABLE 3

| EXAMPLE NO. | | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|
| PROFAX | | 0 | 0 | 0 | 0 | 0 | 0 | 0 | 0 | 0 | 0 | 0 | 0 | 0 | 0 | 17 | 17 | 17 |
| KANEKA | MMBS | 0 | 0 | 0 | 0 | 0 | 0 | 0 | 0 | 0 | 0 | 0 | 0 | 17 | 17 | 0 | 0 | 0 |
| DPDA | 6181 | 0 | 0 | 0 | 0 | 0 | 0 | 0 | 0 | 0 | 17 | 17 | 17 | 0 | 0 | 0 | 0 | 0 |
| MARLEX | 6003 | 0 | 0 | 0 | 0 | 0 | 0 | 17 | 17 | 17 | 0 | 0 | 0 | 0 | 0 | 0 | 0 | 0 |
| SCLAIR | 8405UV | 0 | 0 | 0 | 17 | 17 | 17 | 0 | 0 | 0 | 0 | 0 | 0 | 0 | 0 | 0 | 0 | 0 |
| ELVAX | 460 | 17 | 17 | 17 | 0 | 0 | 0 | 0 | 0 | 0 | 0 | 0 | 0 | 0 | 0 | 0 | 0 | 0 |
| SWS | 721 | 0 | 0 | 3 | 0 | 0 | 3 | 0 | 0 | 3 | 0 | 0 | 3 | 0 | 0 | 0 | 0 | 3 |
| GE | 5530 | 0 | 3 | 0 | 0 | 3 | 0 | 0 | 3 | 0 | 0 | 3 | 0 | 0 | 3 | 0 | 3 | 0 |
| GE | 3320 | 3 | 0 | 0 | 3 | 0 | 0 | 3 | 0 | 0 | 3 | 0 | 0 | 3 | 0 | 3 | 0 | 0 |
| HUELS | 4006 | 78.2 | 78.2 | 78.2 | 78.2 | 78.2 | 78.2 | 78.2 | 78.2 | 78.2 | 78.2 | 78.2 | 78.2 | 78.2 | 78.2 | 78.2 | 78.2 | 78.2 |
| UNBEAMED TEST DATA | | | | | | | | | | | | | | | | | | |
| TENSILE PSI | | 1041 | 1193 | 1194 | 1119 | 1082 | 1383 | 1167 | 1282 | 1386 | 1046 | 1353 | 1279 | 1200 | 1117 | 975 | 892 | 1286 |
| % ELONGATION | | 195 | 270 | 400 | 135 | 5 | 445 | 20 | 155 | 335 | 315 | 450 | 400 | 116 | 145 | 60 | 150 | 215 |
| BEAMED TEST DATA | | | | | | | | | | | | | | | | | | |
| TENSILE PSI | | 1621 | 1705 | 2440 | 1200 | 1944 | 1128 | 1576 | 2348 | 2193 | 111 | 2058 | 2201 | | | 1626 | 1613 | 1575 |
| % ELONGATION | | 220 | 250 | 340 | 70 | 270 | 70 | 100 | 220 | 300 | 200 | 250 | 360 | | | 25 | 60 | 45 |
| M100 PSI | | 51 | 74 | 62 | 58 | 65 | 51 | 58 | 47 | 59 | 46 | 50 | 48 | | | 40 | 44 | 6 |

TABLE 4

| EXAMPLE NO. | | 45 | 46 | 47 | 48 | 49 | 50 | 51 | 52 |
|---|---|---|---|---|---|---|---|---|---|
| PROFAX | | 0 | 0 | 0 | 0 | 0 | 17 | 17 | 17 |
| AESNO-TL | | 0 | 0 | 0 | 17 | 17 | 0 | 0 | 0 |
| KANEKA | MMBS | 17 | 17 | 17 | 0 | 0 | 0 | 0 | 0 |
| SWS | 721 | 0 | 0 | 3 | 0 | 0 | 0 | 0 | 3 |
| GE | 5530 | 0 | 3 | 0 | 0 | 3 | 0 | 3 | 0 |
| GE | 3320 | 3 | 0 | 0 | 3 | 0 | 3 | 0 | 0 |
| HYTREL | | 78.2 | 78.2 | 78.2 | 78.2 | 78.2 | 78.2 | 78.2 | 78.2 |
| UNBEAMED TEST DATA | | | | | | | | | |
| TENSILE PSI | | 2590 | 2581 | 2024 | 2171 | 2343 | 2021 | 2600 | 2092 |
| % ELONGATION | | 620 | 580 | 510 | 580 | 640 | 625 | 765 | 580 |
| BEAMED TEST DATA | | | | | | | | | |
| TENSILE PSI | | | | | 1840 | 3527 | 1804 | 2639 | 3522 |
| % ELONGATION | | | | | 460 | 430 | 425 | 800+ | 615 |
| M100 PSI | | | | | 75 | 69 | 31 | 26 | 34 |

TABLE 5

| EXAMPLE NO. | | 53 | 54 | 55 | 56 | 57 | 58 | 59 | 60 | 61 | 62 | 63 | 64 | 65 | 66 |
|---|---|---|---|---|---|---|---|---|---|---|---|---|---|---|---|
| MARLEX | 6003 | 17 | 15 | 20 | 25 | 30 | 35 | 18.5 | 18.5 | 18.5 | 0 | 0 | 0 | 0 | 0 |
| DFD | 6040 | 0 | 0 | 0 | 0 | 0 | 0 | 0 | 0 | 0 | 17 | 17 | 17 | 17 | 17 |
| SWS | 721 | 0 | 0 | 0 | 0 | 0 | 0 | 0 | 0 | 0 | 3 | 0 | 0 | 0 | 0 |
| GE | 5530 | 6 | 3 | 3 | 3 | 3 | 6 | 0 | 0 | 0 | 0 | 3 | 0 | 3 | 3 |
| GE | 3320 | 0 | 0 | 0 | 0 | 0 | 0 | 0 | 0 | 0 | 0 | 0 | 3 | 0 | 0 |
| HYTREL | | 75.2 | 80.2 | 75.8 | 70.2 | 65.2 | 57.2 | 79.7 | 0 | 0 | 78.2 | 78.2 | 78.2 | 0 | 0 |
| KRATON | G2705 | 0 | 0 | 0 | 0 | 0 | 0 | 0 | 79.7 | 0 | 0 | 0 | 0 | 78.2 | 0 |
| HUELS | 4006 | 0 | 0 | 0 | 0 | 0 | 0 | 0 | 0 | 79.7 | 0 | 0 | 0 | 0 | 78.2 |
| UNBEAMED TEST DATA | | | | | | | | | | | | | | | |
| TENSILE PSI | | 3427 | 3024 | 2774 | 2672 | 2622 | 1429 | 2703 | 2917 | 4960 | 3299 | 3710 | 3377 | 1812 | 1472 |

TABLE 5-continued

| EXAMPLE NO. | 53 | 54 | 55 | 56 | 57 | 58 | 59 | 60 | 61 | 62 | 63 | 64 | 65 | 66 |
|---|---|---|---|---|---|---|---|---|---|---|---|---|---|---|
| % ELONGATION | 845 | 795 | 750 | 775 | 785 | 630 | 770 | 855 | 400 | 880 | 870 | 820 | 760 | 515 |
| BEAMED TEST DATA | | | | | | | | | | | | | | |
| TENSILE PSI | 2744 | 3216 | 2903 | 2707 | 2767 | 2725 | 3414 | 1781 | 4299 | 3804 | 3204 | 3015 | 1526 | 2313 |
| % ELONGATION | 535 | 590 | 550 | 465 | 475 | 400 | 560 | 690 | 325 | 690 | 655 | 615 | 755 | 300 |
| M100 PSI | 61 | 65 | 64 | 61 | 67 | 64 | 75 | 18 | 62 | 49 | 46 | 47 | 9 | 40 |

TABLE 6

| EXAMPLE NO. | | 67 | 68 | 69 | 70 | 71 | 72 | 73 | 74 | 75 | 76 |
|---|---|---|---|---|---|---|---|---|---|---|---|
| MARLEX | 6003 | 17 | 17 | 15 | 15 | 20 | 20 | 25 | 25 | 30 | 30 |
| GE | 5530 | 6 | 6 | 3 | 3 | 3 | 3 | 3 | 3 | 3 | 3 |
| KRATON | G2705 | 75.2 | 0 | 80.2 | 0 | 75.2 | 0 | 70.2 | 0 | 65.2 | 0 |
| HUELS | 4006 | 0 | 75.2 | 0 | 80.2 | 0 | 75.2 | 0 | 70.2 | 0 | 65.2 |
| UNBEAMED TEST DATA | | | | | | | | | | | |
| TENSILE PSI | | 2281 | 1101 | 2800 | 1338 | 2360 | NA | 2436 | NA | 2950 | NA |
| % ELONGATION | | 765 | 0 | 845 | 385 | 705 | 0 | 780 | 0 | 815 | 0 |
| BEAMED TEST DATA | | | | | | | | | | | |
| TENSILE PSI | | 1466 | 1601 | 1552 | 2140 | 1649 | 1600 | 2100 | 1677 | 1969 | 1381 |
| % ELONGATION | | 715 | 110 | 745 | 280 | 810 | 0 | 740 | 0 | 680 | 0 |
| M100 PSI | | 8 | 46 | 8 | 44 | 9 | NA | 14 | NA | 13 | NA |

TABLE 7

| EXAMPLE NO. | | 77 | 78 | 79 | 80 | 81 | 82 | 83 | 84 | 85 | 86 | 87 | 88 |
|---|---|---|---|---|---|---|---|---|---|---|---|---|---|
| MARLEX | 6003 | 0 | 0 | 0 | 0 | 17 | 0 | 0 | 0 | 0 | 0 | 0 | 0 |
| DFD | 6040 | 0 | 0 | 0 | 0 | 0 | 17 | 0 | 0 | 0 | 17 | 17 | 17 |
| GULF | 2205 | 0 | 0 | 0 | 0 | 0 | 0 | 17 | 17 | 17 | 0 | 0 | 0 |
| SWS | C154 | 0 | 0 | 0 | 0 | 0 | 0 | 0 | 0 | 0 | 3 | 3 | 3 |
| GE | 5530 | 0 | 0 | 0 | 0 | 3 | 3 | 3 | 3 | 3 | 0 | 0 | 0 |
| HYTREL | | 0 | 98.2 | 0 | 0 | 0 | 0 | 78.2 | 0 | 0 | 78.2 | 0 | 0 |
| KRATON | G2705 | 0 | 0 | 98.2 | 0 | 0 | 0 | 0 | 0 | 78.2 | 0 | 0 | 78.2 |
| HUELS | 4006 | 98.2 | 0 | 0 | 0 | 0 | 0 | 0 | 78.2 | 0 | 0 | 78.2 | 0 |
| SURLYN | AD8231 | 0 | 0 | 0 | 98.2 | 78.2 | 78.2 | 0 | 0 | 0 | 0 | 0 | 0 |
| UNBEAMED TEST DATA | | | | | | | | | | | | | |
| TENSILE PSI | | 2800 | 3847 | 1995 | 4255 | 4233 | 3823 | 4080 | 1491 | 1527 | 3520 | 1368 | 2000 |
| % ELONGATION | | 655 | 800 | 825 | 430 | 670 | 435 | 840 | 465 | 760 | 820 | 440 | 770 |
| BEAMED TEST DATA | | | | | | | | | | | | | |
| TENSILE PSI | | 3127 | 5768 | 1434 | 5043 | 5485 | 4445 | 3704 | 2269 | 1433 | 3753 | 2513 | 1621 |
| % ELONGATION | | 430 | 725 | 860 | 290 | 330 | 280 | 595 | 330 | 765 | 660 | 370 | 740 |
| M100 PSI | | 34 | 21 | 0 | 60 | 61 | 78 | 34 | 39 | 4 | 32 | 33 | 8 |

We claim:

1. A polymeric composition which comprises
   (a) 12 to 40% by weight of a thermoplastic polymer comprising units derived from an olefin,
   (b) 1 to 10% by weight of a polymer which is solid at room temperature and which is a block copolymer comprising polysiloxane blocks and at least 10% by weight of polycarbonate blocks, and
   (c) 48 to 88% by weight of a styrene-butadiene elastomer having a Shore D Hardness of less than 60,
   the amounts of components (a), (b) and (c) being by weight, based on the total weight of (a), (b) and (c).

2. A composition according to claim 1 wherein the polymer (b) comprises poly(dimethyl siloxane) blocks and polycarbonate blocks derived from Bisphenol-A.

* * * * *